United States Patent [19]

Pinchuk

[11] Patent Number: 4,851,009
[45] Date of Patent: Jul. 25, 1989

[54] CRACK PREVENTION OF IMPLANTED PROSTHESES

[75] Inventor: Leonard Pinchuk, Miami, Fla.

[73] Assignee: Corvita Corporation, Miami, Fla.

[21] Appl. No.: 210,145

[22] Filed: Jun. 15, 1988

Related U.S. Application Data

[63] Continuation of Ser. No. 809,926, Dec. 16, 1985, abandoned.

[51] Int. Cl.$^4$ ............................................. A61F 2/54
[52] U.S. Cl. ........................................ 623/66; 623/1;
  623/11; 427/2; 128/419 P; 128/335.5
[58] Field of Search ............... 128/419 P, DIG. 21,
  128/335.5; 623/1, 11, 66, 6; 427/2

[56] References Cited

U.S. PATENT DOCUMENTS

| | | | |
|---|---|---|---|
| 2,609,320 | 9/1952 | Modigliani | 623/1 |
| 3,187,752 | 6/1965 | Glick | 427/2 |
| 3,434,869 | 3/1969 | Davidson | 427/2 |
| 3,527,556 | 9/1970 | Riley | 128/335.5 |
| 3,629,358 | 12/1971 | Lamoreaux et al. | 623/66 |
| 3,683,424 | 8/1972 | Pangman | 128/DIG. 21 |
| 3,708,324 | 1/1973 | Stebleton | 623/1 |
| 3,729,007 | 4/1973 | Mirkovitch | 128/335.5 |
| 4,156,067 | 5/1979 | Gould | 128/334 R |
| 4,475,972 | 10/1984 | Wong | 623/1 |
| 4,595,610 | 6/1986 | Fey | 427/387 |
| 4,608,428 | 8/1986 | Shalaby et al. | 128/335.5 |
| 4,687,482 | 8/1987 | Hanson | 623/9 |

FOREIGN PATENT DOCUMENTS

| | | | |
|---|---|---|---|
| 2183757 | 8/1987 | Japan | 623/1 |
| 0562278 | 6/1977 | U.S.S.R. | |
| 2140437 | 11/1984 | United Kingdom | 623/1 |

OTHER PUBLICATIONS

Sax et al., Hawley's Condensed Chemical Dictionary, 11th Ed., (1987, 1981, 1971), p. 574.
"Failed Pacemaker Leads", Hearing before Congressional Subcommittee on Oversight and Investigations, 98th Congress, 2nd Session, Serial No. 98-134, Mar. 13, 1984.
"Thermal Plastic Polyurethanes as Insulating Materials for Long-Life Cardiac Pacing Leads", Pande, PACE, vol. 6, Sep.-Oct. 1983, Part I, pp. 858-867.
"Biocompatability of Intraocular Lens Polymers", Goldberg et al, Apr. 1985.

*Primary Examiner*—Richard J. Apley
*Assistant Examiner*—Paul Prebilic
*Attorney, Agent, or Firm*—Lockwood, Alex, FitzGibbon & Cummings

[57] ABSTRACT

Implantable devices having a biocompatible polymeric surface which is elastomeric and susceptible to cracking under in vivo conditions are provided which have been subjected to treatment with a crack preventative composition that includes an elastomeric silicone such as poly(dimethyl siloxane). This treatment substantially prevents cracking of the implantable device after it is implanted.

18 Claims, 1 Drawing Sheet

CRACK PREVENTION OF IMPLANTED PROSTHESES

This is a continuation of application Ser. No. 809,926 filed Dec. 16, 1985, now abandoned.

BACKGROUND AND DESCRIPTION OF THE INVENTION

The present invention generally relates to implantable prostheses and to methods for making and treating same in order to substantially prevent cracking or crazing thereof when they are implanted, the treatment including applying a silicone rubber material to an implantable polymeric surface of a medical prosthesis, the polymeric surface being one that will crack when subjected to implantation for substantial time periods if it is not thus treated with the silicone rubber material. The implantable polymeric surface is made of a material that has a surface tension which is greater than that of the silicone rubber, the silicone rubber being a substantially non-polar material which is conveniently applied by immersing the medical prosthesis to be treated into a composition containing the silicone rubber.

Several biocompatible materials which are quite suitable for use in making implantable medical devices that may be broadly characterized as implantable prostheses exhibit properties that are sought after in such devices, including one or more of exceptional biocompatibility, extrudability, moldability, good fiber forming properties, tensile strength, elasticity, durability and the like. However, some of these otherwise highly desirable materials exhibit a serious deficiency when implanted within the human body or the like, such deficiency being the development of strength reducing and unsightly cracks which, for prostheses components having relatively thin strands or members, cause a complete severance of a number of those strands or members. Often, surface fissuring or cracking occurs after substantial exposure, which may be on the order of one month or more or shorter time periods depending upon the materials and the conditions, to body fluids such as are encountered during in vivo implantation and use. Many implantable prostheses are intended to be permanent in nature and should not develop any substantial cracking during years of implantation.

Several theories have been promulgated in attempting to define the cause of this cracking phenomenon. Proposed mechanisms include oxidative degradation, hydrolytic instability, enzymatic destruction, thermal and mechanical failure, immunochemical mechanisms and imbibition of lipids. Prior attempts to control surface fissuring or cracking upon implantation include incorporating antioxidants within the biocompatible polymer and subjecting the biocompatible polymer to various different annealing conditions, typically including attempting to remove stresses within the polymer by application of various heating and cooling conditions. Attempts such as these have been largely unsuccessful.

A particular need in this regard is evident when attempting to form prostheses with procedures including the extrusion or spinning of polymeric fibers, such as are involved in winding fiber-forming polymers into porous vascular grafts, for example as described in U.S. Pat. No. 4,475,972, the subject matter thereof being incorporated by reference hereinto. Such vascular grafts include a plurality of strands that are of a somewhat fine diameter size such that, when cracking develops after implantation, this cracking often manifests itself in the form of complete severance of various strands of the vascular graft. Such strand severance cannot be tolerated to any substantial degree and still hope to provide a vascular graft that can be successfully implanted on a generally permanent basis whereby the vascular graft remains viable for a number of years.

Numerous vascular graft structures that are made from spun fibers appear to perform very satisfactorily insofar as their viability when subjected to physical stress conditions that approximate those experienced during and after implantation, including stresses imparted by sutures and the like. For example, certain polyurethane fibers, when subjected to constant stress under in vitro conditions, such as in saline solution at body temperatures, do not demonstrate cracking that is evident when substantially the same polyurethane spun vascular graft is subjected to in vivo conditions. Accordingly, while many materials, such as polyurethanes, polypropylenes, polymethylmethacrylate and the like, may appear to provide superior medical devices or prostheses when subjected to stresses under in vitro conditions are found to be less than satisfactory when subjected to substantially the same types of stresses but under in vivo conditions.

There is accordingly a need for a treatment which will impart crack preventative properties to polymers that experience surface fissuring or cracking under implanted or in vivo conditions and which are otherwise desirable and advantageous in connection with the formation of medical devices or prostheses that must successfully thwart the cracking phenomenon even after implantation for months and years, in many cases a substantial number of years. Exemplary medical devices or prostheses for which such a treatment would be significantly advantageous include vascular grafts, intraocular lens loops or haptics, pacemaker lead insulators, permanent sutures, diaphragms for artificial hearts, prosthetic heart valves, and the like. Moreover, experience has shown that crack prevention that is successful under in vitro conditions is not necessarily successful under in vivo conditions.

Objectives of this type are met by the present invention which achieves a successful treatment of biocompatible polymers including polyurethanes, polypropylenes, polymethylmethacrylate and the like to the extent that these polymers do not exhibit the surface fissuring, cracking or crazing phenomenon which they would otherwise exhibit under in vivo conditions. The invention includes treating such polymers with a crack preventative material that includes a silicone rubber, typically a siloxane. The treatment can be carried out by a procedure as straightforward as dipping the prosthesis into a container including the silicone rubber material and a crosslinker or curing agent, preferably followed by taking steps to insure that the silicone rubber material adsorbs into and on the biocompatible surface of the prosthetic device at least to the extent that the crack preventative is secured to the biocompatible surface of the implantable device or medical prosthesis. Alternatively, the biocompatible surface can be pretreated with primer or other material or radiation that provides the surface with chemical functionality with which the silicone rubber material can react and to which it can bond.

It is accordingly a general object of the present invention to provide an improved implantable device, method of its production, and crack prevention treatment.

Another object of this invention is to provide an improved vascular graft that is made from spun fibers and that exhibits an exceptional ability to prevent the formation of cracks and strand severances upon implantation for substantial time periods such as those experienced in generally permanent implantation procedures.

Another object of the present invention is to provide an improved crack preventative treatment procedure for biocompatible polymers having a surface tension greater than that of a silicone rubber crack preventative agent.

Another object of the present invention is to provide an improved production method, treatment method and treated product that imparts in vivo crack prevention properties to biocompatible polymeric materials that exhibit desirable medical properties but experience cracking in in vivo applications.

Another object of this invention is to provide an improved treatment method, product and process for preparation thereof which dramatically improves the crack resistance properties of a biocompatible material while also imparting lubricating or friction reduction properties thereto.

These and other objects, features and advantages of this invention will be clearly understood through a consideration of the following detailed description.

BRIEF DESCRIPTION OF THE DRAWINGS

In the course of this description, reference will be made to the attached drawings, wherein.

DESCRIPTION OF THE PARTICULAR EMBODIMENTS

Figure 1:
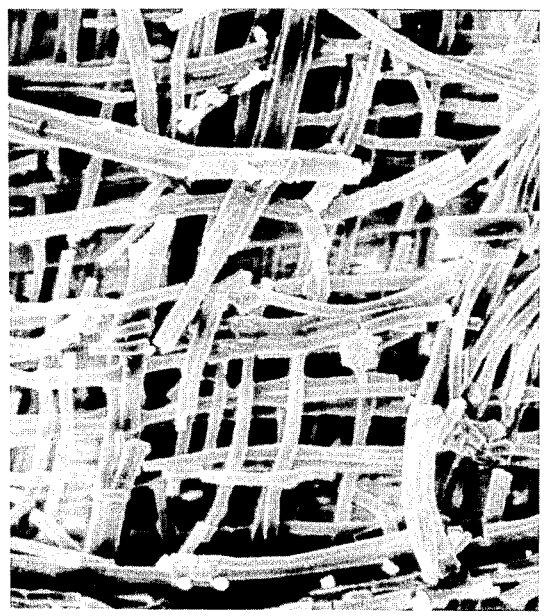
FIG. 1 is a photomicrograph of a section of a vascular graft made by spinning a polyurethane not treated in accordance with this invention and after subcutaneous implantation.

Crack preventative materials in accordance with the present invention are of the silicone rubber type and are most typically and readily provided within crack preventative compositions that include a silicone rubber type of material and a solvent therefor. Often, the crack preventative composition includes a catalyst and a crosslinker or other system for curing the silicone rubber type of material. A convenient manner of incorporating the silicone rubber type of material into the crack preventative composition is to provide same in dispersion form. Thinning agents, actinic radiation, coupling agents and primer coatings for the silicone rubber type of material may also be utilized.

With more particular reference to the crack preventative agent itself, this silicone rubber type of component is preferably a siloxane having groups which can be generally represented by the formula:

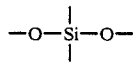

A representative siloxane component, prior to curing, can be represented by the formula:

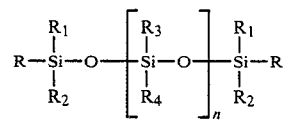

wherein each of R, $R_1$ and/or $R_2$ can be a group such as an ester moiety, an acetoxy moiety, an alcohol moiety, an acrylic moiety and the like that are involved in the crosslinking, curing or polymerizing of the siloxane component. $R_3$ and $R_4$, as well as $R_1$ and $R_2$, can each be aliphatic or aromatic groups such as methyl, ethyl, propyl, phenyl, or substituted aliphatics or aromatics containing halogen moieties or other groups, for example 3,3,3-trifluoropropylmethyl moieties. This general formula represents a siloxane component that can react with itself with or without the presence of moisture and/or a catalyst in order to crosslink or polymerize into the silicone elastomer. If at least the R groups are alcohol moieties, the silicone elastomer can be formed by reaction with a suitable crosslinking component.

An exemplary silicone elastomer or rubber is a siloxane condensation reaction product, the principal reactants of which include a silicone moiety:

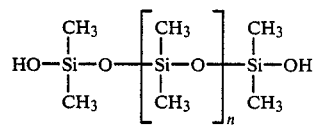

wherein n has an average value of greater than 100. Another principal reactant is an acetoxy silane crosslinker of the formula:

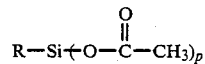

wherein p is 1, 2 or 3. The exemplary siloxane of this type is poly(dimethyl siloxane). Other siloxane polymers include poly(ethylmethyl siloxane), poly(3,3,3-trifluoropropylmethyl siloxane) and copolymers of these types of siloxanes with poly(dimethyl siloxane). Polymeric siloxanes are generally known and are available commercially, for example, from Dow Corning Corporation. Siloxanes are generally described in U.S. Pat. No. 3,434,869, the subject matter of which is incorporated by reference hereinto. These materials are hydrophobic and substantially non-polar.

Usually these silicone rubber or silicone resin materials will be applied in accordance with this invention while dispersed or dissolved in a solvent that will not detrimentally affect the surface of the implanted device that is being treated. Typically acceptable solvents in this regard include heptane, hexamethyldisiloxane, trichloroethane, polyhalogenated hydrocarbons and the like. Exemplary polyhalogenated hydrocarbons include materials available under the Freon trademark, including trichlorofluoromethane, dichlorodifluoromethane, 1,2-dichloro-1,1,2,2-tetrafluoroethane and octafluorocyclobutane. Certain of these polyhalogenated hydrocarbons exhibit atmospheric boiling points below room temperature, and these solvents can be advantageously used by maintaining the application composition at an appropriate elevated pressure and/or decreased temperature so that the solvent is liquid during application and readily evaporates thereafter.

These silicone rubbers perform best when crosslinked, and crosslinking is facilitated by a suitable catalyst, although curing at room temperature and at elevated temperatures with ultraviolet or gamma radiation can also be practiced. Suitable crosslinkers containing catalysts are available commerically, for example from Dow Corning Corporation and are typically combined with the silicone polymer dispersion at a ratio of on the order of 50:1 silicone rubber dispersion to crosslinker/catalyst, the ratio being by weight. Exemplary catalysts are those including platinum, benzoil peroxide, tin, and the like.

Usually, especially when the implantable device being treated consists of one or more fine strands, the crack preventative will adequately adhere to the bicompatible surface of the implantable device without the need of any pretreatment thereof. In those instances where the implantable device has a relatively large and smooth surface area, such as would be the case for a cardiac pacer lead insulator or an artificial heart diaphragm which present a unitary surface area that is generally smooth and without any significant undulations or porosity. In these instances, it can be advantageous to pretreat the surface of the implantable device with a coupling agent or primer coating such as the priming solution that is described in U.S. Pat. No. 3,434,869, including the primers specified therein which are reaction products of aminoorganosilicon compounds and epoxy resins. Others include mercaptosilanes. Typical coupling agent or primer coating compositions include such primers in solution or dispersion with solvents including isopropanol, acetone, water and the like. Components such as methyltrimethoxy silane can be added to enhance the priming properties. A thin film of the coupling agent or primer composition is typically sitable and may be applied by brushing, dipping, spraying or the like.

Bonding between the substrate and the silicone polymer, or grafting of the silicone onto the substrate can also be facilitated by exposing the substrate/silicone system to a suitable free radical initiator. Exemplary silicones for this application include those containing acrylic functional groups or crosslinkers with acrylic functionality. Typical initiators include actinic radiation such as ultraviolet light, RF Plasma sources, gamma radiation, high temperature, or the like or combinations of the above. Known radiation initiators include oxidizing agents such as ceric ammonium nitrate and the like.

Whether or not pretreatment is performed, the implantable device or portion thereof to be rendered resistant to in vivo crack development is contacted with the crack preventative composition, typically by immersion into a bath of the crack preventative composition, although spraying, brushing or the like could also be used. After such application of the crack preventative composition, it is usually preferred to physically manipulate the device in order to remove excess crack preventative composition and to assist in directing the crack preventative into interstices or undulations of the device. Exemplary physical manipulations in this regard include one or more of squeezing the device such as between rollers or presses, utilizing a vacuum system or a centrifuge device, use of increased quantities of diluents in the crack preventative composition, or the like.

The diluents and/or solvents should be evaporated or otherwise removed. Thorough coverage may require repetitive coatings if so desired.

Application of the crack preventative can include or be closely followed by a curing operation, whether in conjunction with a suitable catalyst with a crosslinker as herein described or in association with a vulcanizing type of procedure at ambient or at elevated temperatures. Moisture levels can also contribute to the effectiveness of such post-treatment procedures.

The crack preventative treatments according to this invention are used to form or provide implantable devices having biocompatible surfaces that are substantially completely crack-free and that will not crack or sever after having been implanted for extensive time periods. Implantable medical devices that are especially appropriate products according to this invention are vascular grafts that are spun from extruded fibers on an apparatus including an elongated mandrel and a spinnerette assembly that rotate with respect to each other while the spinnerette traverses a pathway generally along the elongated mandrel. Other especially appropriate products include permanent sutures, especially since crack development in such products can lead to breakage of the permanent suture and a diminishment of its intended implanted function. Other especially appropriate products include the loops or haptics of intraocular lens implants. The products according to this invention can also include items such as the external insulator sheath of cardiac pacemaker leads, artificial heart diaphragms, artificial heart valve leaflets and sewing cuffs, and the like. These products also exhibit a beneficial additional property of typically exhibiting reduced surface friction, which can be especially evident when suturing a vascular graft treated according to this invention wherein the suture readily slides with respect to strands of the vascular graft through which it is passed in order to facilitate the ability of the surgeon to slide the vascular graft to its desired surgical implant location by pulling on the suture.

Materials out of which these implantable medical devices may be made include substantially any biocompatible material, typically a polymeric material, which has a surface tension that is greater than that of the crack preventative material, primarily in order to effect proper adsorption of the crack preventative onto the biocompatible material. For example, a typical siloxane has a surface tension of approximately 18 Dynes/cm, and biocompatible materials having a surface tension greater than this value would be suitable. Included are various polyurethanes, polypropylenes and acrylate polymers such as polymethylmethacrylate. Exemplary polyurethanes include polyurethanes and poly(fluorosilicone urethane) copolymers, which are described in my copending application entitled "Polyurethanes". Such materials may be subjected to annealing conditions prior to treatment with the crack preventative composition.

EXAMPLE

A polyurethane dissolved in dimethyl acetamide was spun onto a rotating mandrel in the manner generally described in U.S. Pat. No. 4,475,972 in order to form a vascular graft having individual fibers with a diameter of approximately 8 microns. The resulting graft was annealed for 48 hours under alternating atmospheres of nitrogen and vacuum at 80° C. and then cut into separate pieces or segments. Two of these segments were not further modified and served as unmodified controls. Another two of these separate segments were subjected to the crack preventative procedure in accordance with this invention.

More particularly, the two treated segments were subjected to silicone impregnation which included forming a crack preventative composition including a 50:1 by weight mixture of a Dow Corning silicone dispersion with the recommended Dow Corning catalyst. These two graft segments were then submerged into this crack preventative composition, and the mixture was evacuated for two to ten minutes to remove air bubbles and to force the crack preventative composition into the interstices of the graft, after which the two segments of graft were squeezed between two rollers in order to remove excess crack preventative composition. The thus treated graft segments were then dried and cured in a laminar flow hood at room temperature (24° C.) and humidity (40% relative humidity) for 24 hours.

Figure 2:
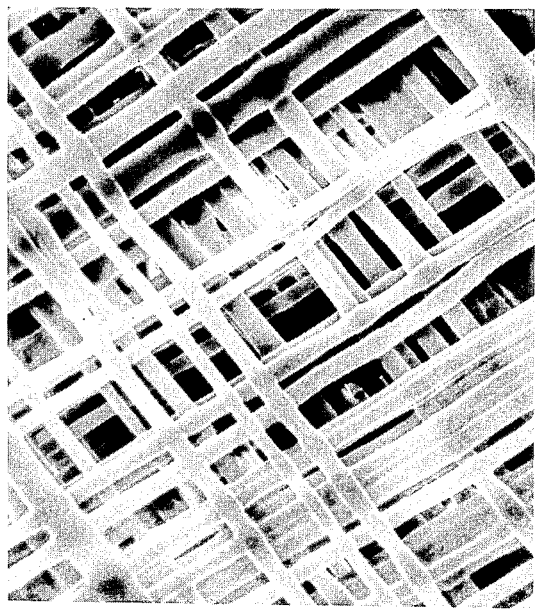
FIG. 2 is a photomicrograph of another section from the spun polyurethane graft used in FIG. 1 but which was treated in accordance with this invention prior to subcutaneous implantation.

The two unmodified control graft segments and the two crack preventative treated segments were ethylene oxide sterilized and implanted subcutaneously in a dog. After one month, all four of the samples were explanted, cleaned in sodium hydroxide and sodium hypochloride solution and then examined under a scanning electron miroscope for fiber breakage and cracking. FIG. 1 is a photomicrograph of the scanning electron microscopic reproduction of a typical unmodified control graft that is not in accordance with this invention, from which obvious cracking and strand breakage are evident, even though such grafts had been subjected to annealing conditions in an effort to reduce cracking and breakage. FIG. 2 is a photomicrograph of the scanning electron microscopic image that is typical of one of the graft sections treated in accordance with this invention. Fiber breakage is essentially non-existent, and no surface cracking can be seen.

Sections of the explanted graft were also manually pulled until breakage was evident, and their relative respective tensile strengths were observed. The unmodified sections exhibited what amounted to an almost complete loss of tensile strength, while the tensile strength of the explanted sections that had been treated in accordance with this invention demonstrated a tensile strength substantially the same as the tensile strength of a section of the graft that was neither implanted nor treated.

It will be understood that the embodiments of the present invention which have been described are illustrative of some of the applications of the principles of the present invention. Numerous modifications may be made by those skilled in the art without departing from the true spirit and scope of the invention.

What is claimed is:

1. A method for forming an implantable device for medical use, which device is treated to substantially prevent in vivo cracking thereof, the method comprising:

providing a non-woven shaped substrate of an implantable medical device having a biocompatible polymeric surface that is elastomeric and susceptible to cracking when subjected to implantation under in vivo conditions for substantial time periods, said in vivo conditions including those that promote crack-forming degradation of said biocompatible polymeric surface, wherein said biocompatible polymeric surface is a polyurethane;

applying a crack preventative composition to said elastomeric biocompatible polymeric surface, said crack preventative composition including a silicone material being a siloxane including

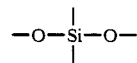

groups and, when polymerized, being elastomeric and having a predetermined surface tension, said applying step including efecting adsorption of the silicone material onto the biocompatible polymeric surface and bonding between said elastomeric silicone material and said elastomeric biocompatible polymeric surface so as to effect grafting of said polymerized elastomeric silicone material onto said elastomeric biocompatible polymeric surface; and said providing step includes selecting said elastomeric biocompatible polymeric surface to have a surface tension that is greater than the predetermined surface tension of said silicone material.

2. The method according to claim 1, wherein said silicone rubber material of the crack preventative composition is a siloxane condensation reaction product of reactants including:

(a) a silicone moiety of the formula:

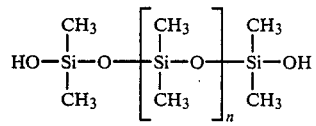

wherein n has an average value of greater than 100; and (b) an acetoxy silane crosslinker,

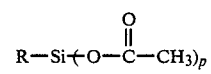

whereby the reaction product is a poly(dimethyl siloxane).

3. The treatment method according to claim 1, wherein said crack preventative composition includes a solvent that does not detrimentally affect said biocompatible polymeric surface.

4. The treatment method according to claim 1, wherein said applying step includes imparting lubricating properties to the biocompatible polymeric surface.

5. The method according to claim 1, wherein said silicone rubber material of the crack preventative composition is a siloxane which, prior to curing, has the formula:

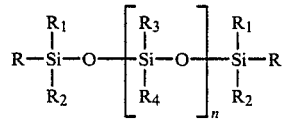

wherein each R group is an organic moiety selected from the group consisting of one or more ester moieties, acetoxy moieties, acrylic moieties and alcohol moieties, wherein each $R_3$ and $R_4$ group is an organic group selected from the group consisting of aliphatic groups and substituted aliphatic groups having from 1 to about 12 carbon atoms, and aromatic groups and substituted aromatic groups having from 6 to about 20 carbon atoms, and wherein each $R_1$ group and $R_2$ group is an organic component selected from the group consisting of R, $R_3$ and $R_4$.

6. The method according to claim 1, wherein said silicone material of the crack preventative composition is poly(dimethyl siloxane).

7. A method for forming an implantable device for medical use, which device is treated to substantially prevent in vivo cracking thereof, the method comprising:
providing a non-woven shaped substrate of an implantable medical device having a biocompatible polymeric surface that is elastomeric and susceptible to cracking when subjected to implantation under in vivo conditions for substantial time periods, said in vivo conditions including those that promote crack-forming degradation of said biocompatible polymeric surface, wherein said shaped substrate includes one or more extruded fibers that are shaped by winding over a mandrel;
applying a crack preventative composition to said elastomeric biocompatible polymeric surface, said crack preventative composition including a silicone material being a siloxane including

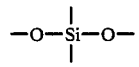

groups and, when polymerized, being elastomeric and having a predetermined surface tension, said applying step including effecting adsorption of the silicone material onto the biocompatible polymeric surface and bonding between said elastomeric silicone material and said elastomeric biocompatible polymeric surface so as to effect grafting of said polymerized elastomeric silicone material onto said elastomeric biocompatible polymeric surface; and
said providing step includes selecting said elastomeric biocompatible polymeric surface to have a surface tension that is greater than the predetermined surface tension of said silicone material.

8. A method for forming an implantable device for medical use, which device is treated to substantially prevent in vivo cracking thereof, the method comprising:
providing a non-woven shaped substrate of an implantable medical device having a biocompatible polymeric surface that is elastomeric and susceptible to cracking when subjected to implantation under in vivo conditions for substantial time periods, said in vivo conditions including those that promote crack-forming degradation of said biocompatible polymeric surface, wherein said shaped substrate includes one or more strands of said biocompatible polymer;
applying a crack preventative composition to said elastomeric biocompatible polymeric surface, said crack preventative composition including a silicone material being a siloxane including

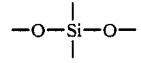

groups and, when polymerized, being elastomeric and having a predetermined surface tension, said applying step including effecting adsorption of the silicone material onto the biocompatible polymeric surface and bonding between said elastomeric silicone material and said elastomeric biocompatible polymeric surface so as to effect grafting of said polymerized elastomeric silicone material onto said elastomeric biocompatible polymeric surface; and
said providing step includes selecting said elastomeric biocompatible polymeric surface to have a surface tension that is greater than the predetermined surface tension of said silicone material.

9. An implantable device for medical use under in vivo conditions, comprising:
a shaped substrate of an implantable medical device having a biocompatible polymeric surface that is elastomeric and susceptible to degradation cracking when subjected to implantation under in vivo conditions for substantial time periods;
a crack preventative adsorbed to and grafted onto said substrate so that there is bonding between said elastomeric substrate and said crack preventative, said crack preventative being an elastomeric silicone material having a predetermined surface tension, said crack preventative being a siloxane including recurring

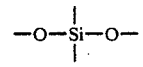

groups;
said biocompatible polymeric surface has a surface tension greater than the predetermined surface tension of the crack preventative; and
said elastomeric biocompatible polymeric surface is a polyurethane.

10. The implantable device according to claim 9, wherein said crack preventative is a siloxane which, prior to curing, has the formula:

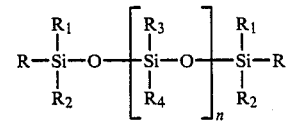

wherein each R group is an organic moiety selected from the group consisting of one or more ester moieties, acetoxy moieties, acrylic moieties and alcohol moieties, wherein each $R_3$ and $R_4$ group is an organic group selected from the group consisting of aliphatic groups and substituted aliphatic groups having from 1 to about 12 carbon atoms, and aromatic groups and substituted aromatic groups having from 6 to about 20 carbon atoms, and wherein each $R_1$ group and $R_2$ group is an organic component selected from the group consisting of R, $R_3$ and $R_4$.

11. The implantable device according to claim 9, wherein said silicone material of the crack preventative composition is poly(dimethyl siloxane).

12. The implantable device according to claim 9, wherein said shaped substrate is a pacemaker lead insulator having a generally smooth surface of said elastomeric biocompatible polymeric material having said crack preventative bonded thereto.

13. An implantable device for medical use under in vivo conditions, comprising:
a shaped substrate of an implantable medical device having a biocompatible polymeric surface that is elastomeric and susceptible to degradation cracking when subjected to implantation under in vivo conditions for substantial time periods, wherein said shaped substrate includes one or more strands of said biocompatible polymer;
a crack preventative adsorbed to and grafted onto said substrate so that there is bonding between said elastomeric substrate and said crack preventative, said crack preventative being an elastomeric silicone material having a predetermined surface tension, said crack preventative being a siloxane including recurring

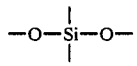

groups; and
said biocompatible polymeric surface has a surface tension greater than the predetermined surface tension of the crack preventative.

14. An implantable device for medical use under in vivo conditions, comprising:
a shaped substrate of an implantable medical device having a biocompatible polymeric surface that is elastomeric and susceptible to degradation cracking when subjected to implantation under in vivo conditions for substantial time periods, wherein said shaped substrate includes one or more extruded fibers that are shaped by winding over a mandrel;
a crack preventative adsorbed to and grafted onto said substrate so that there is bonding between said elastomeric substrate and said crack preventative, said crack preventative being an elastomeric silicone material having a predetermined surface tension, said crack preventative being a siloxane including recurring

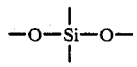

groups; and
said biocompatible polymeric surface has a surface tension greater than the predetermined surface tension of the crack preventative.

15. An implantable device for medical use under in vivo conditions, comprising:
a shaped substrate of an implantable medical device having a biocompatible polymeric surface that is elastomeric and susceptible to degradation cracking when subjected to implantation under in vivo conditions for substantial time periods;
a crack preventative adsorbed to and grafted onto said substrate so that there is bonding between said elastomeric substrate and said crack preventative, said crack preventative being an elastomeric silicone material having a predetermined surface tension, said crack preventative being a siloxane including recurring

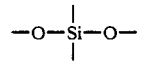

groups;
said biocompatible polymeric surface has a surface tension greater than the predetermined surface tension of the crack preventative; and
said shaped substrate is a graft including wound strands of extruded fiber that overlie and intersect one another, and said extruded fiber is said elastomeric biocompatible polymeric surface having said crack preventative bonded thereto.

16. An implantable device for medical use under in vivo conditions, comprising:
a shaped substrate of an implantable medical device having a biocompatible polymeric surface that is elastomeric and susceptible to degradation cracking when subjected to implantation under in vivo conditions for substantial time periods;
a crack preventative adsorbed to and grafted onto said substrate so that there is bonding between said elastomeric substrate and said crack preventative, said crack preventative being an elastomeric silicone material having a predetermined surface tension, said crack preventative being a siloxane including recurring

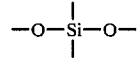

groups;
said biocompatible polymeric surface has a surface tension greater than the predetermined surface tension of the crack preventative; and
said shaped substrate is a suture including an extruded fiber that is composed of said elastomeric biocompatible polymeric surface having said crack preventative bonded thereto.

17. An implantable device for medical use under in vivo conditions, comprising:
a shaped substrate of an implantable medical device having a biocompatible polymeric surface that is elastomeric and susceptible to degradation cracking when subjected to implantation under in vivo conditions for substantial time periods;
a crack preventative adsorbed to and grafted onto said substrate so that there is bonding between said elastomeric substrate and said crack preventative, said crack preventative being an elastomeric silicone material having a predetermined surface tension, said crack preventative being a siloxane including recurring

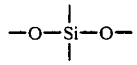

groups;

said biocompatible polymeric surface has a surface tension greater than the predetermined surface tension of the crack preventative; and said elastomeric biocompatible polymeric surface is a polyurethane, and said crack preventative bonded thereto is acetoxy terminated poly(dimethyl siloxane).

18. A method for forming an implantable device for medical use, which device is treated to substantially prevent in vivo cracking thereof, the method comprising:

providing a non-woven shaped substrate of an implantable medical device having a biocompatible polymeric surface that is elastomeric and susceptible to cracking when subjected to implantation under in vivo conditions for substantial time periods, said in vivo conditions including those that promote crack-forming degradation of said biocompatible polymeric surface, wherein said elastomeric biocompatible polymeric surface is a polyurethane, and wherein said crack preventative bonded thereto is acetoxy terminated poly(dimethyl siloxane);

applying a crack preventative composition to said elastomeric biocompatible polymeric surface, said crack preventative composition including a silicone material being a siloxane including

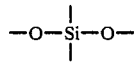

groups and, when polymerized, being elastomeric and having a predetermined surface tension, said applying step including effecting adsorption of the silicone material onto the biocompatible polymeric surface and bonding between said elastomeric silicone material and said elastomeric biocompatible polymeric surface so as to effect grafting of said polymerized elastomeric silicone material onto said elastomeric biocompatible polymeric surface; and said providing step includes selecting said elastomeric biocompatible polymeric surface to have a surface tension that is greater than the predetermined surface tension of said silicone material.

* * * * *

UNITED STATES PATENT AND TRADEMARK OFFICE
CERTIFICATE OF CORRECTION

PATENT NO.   :   4,851,009
DATED        :   July 25, 1989
INVENTOR(S)  :   Leonard Pinchuk It is certified that error appears in the above-identified patent and that said Letters Patent is hereby corrected as shown below:

TITLE PAGE:

In the ABSTRACT, after the last sentence, add: --Preferably, an elastomeric crack preventative, such as silicone, is grafted onto the polymeric substrate so that there is bonding between the elastomeric substrate and the crack preventative. In addition the substrate is selected to have a surface tension which is greater than the crack preventative.--

Col. 5, line 40, "sitable" should read --suitable--.

Col. 8, line 47, delete "treatment"; line 49, "detreimentally" should read --detrimentally--; line 51, delete "treatment".

Signed and Sealed this

Twenty-third Day of April, 1991

Attest:

HARRY F. MANBECK, JR.

Attesting Officer

Commissioner of Patents and Trademarks